(12) United States Patent
El-Khatib et al.

(10) Patent No.: US 10,188,795 B2
(45) Date of Patent: Jan. 29, 2019

(54) BLOOD GLUCOSE CONTROL SYSTEM

(71) Applicants: Trustees of Boston University, Boston, MA (US); The General Hospital Corporation, Boston, MA (US)

(72) Inventors: Firas El-Khatib, Allston, MA (US); Edward Damiano, Acton, MA (US); Steven J. Russell, Lincoln, MA (US)

(73) Assignees: Trustees of Boston University, Boston, MA (US); The General Hospital Corporation, Boston, MA (US)

( * ) Notice: Subject to any disclaimer, the term of this patent is extended or adjusted under 35 U.S.C. 154(b) by 105 days.

(21) Appl. No.: 15/380,516

(22) Filed: Dec. 15, 2016

(65) Prior Publication Data

US 2017/0095612 A1    Apr. 6, 2017

Related U.S. Application Data

(60) Division of application No. 13/870,634, filed on Apr. 25, 2013, now Pat. No. 9,833,570, which is a (Continued)

(51) Int. Cl.
    *A61M 5/172*       (2006.01)
    *G16H 50/50*       (2018.01)
                 (Continued)

(52) U.S. Cl.
    CPC ...... *A61M 5/1723* (2013.01); *A61M 5/14244* (2013.01); *A61M 5/14248* (2013.01);
                 (Continued)

(58) Field of Classification Search
    CPC ...... A61M 5/1723; A61M 2005/14208; A61M 2230/201; A61M 2205/52
See application file for complete search history.

(56) References Cited

U.S. PATENT DOCUMENTS

| | | | |
|---|---|---|---|
| 4,464,170 | A | 8/1984 | Clemens et al. |
| 6,544,212 | B2 | 4/2003 | Galley et al. |
| 7,651,845 | B2 | 1/2010 | Doyle, III et al. |
| 7,766,829 | B2 | 8/2010 | Sloan et al. |
| 7,850,641 | B2 | 12/2010 | Lebel et al. |
| 2007/0282299 | A1 | 12/2007 | Hellwig |

(Continued)

FOREIGN PATENT DOCUMENTS

| | | |
|---|---|---|
| JP | 2007-529241 A | 10/2007 |
| JP | 2008545454 A | 12/2008 |

(Continued)

*Primary Examiner* — Emily L Schmidt
(74) *Attorney, Agent, or Firm* — BainwoodHuang

(57) ABSTRACT

Techniques are used for adaptation of drug-administration parameters that control insulin delivery in a blood glucose control system. One technique provides long-term adaptation of a nominal basal infusion rate, adapting to longer-term changes in a patient's needs due to growth, illness, hormonal fluctuations, physical activity, aging, etc. Another technique provides adaptation of priming dose size at mealtimes for overall better glycemic control and also adapting to longer-term changes in a patient's needs. Adaptation calculations use a receding-horizon window of recent values of the adapted parameter. Doses of a counter-regulatory agent (e.g., glucagon) may also be delivered in response to information about estimated accumulation of exogenously infused insulin (subcutaneously, intramuscularly, intraperitoneally, or intravenously) and/or the effect insulin might have on glucose levels (blood glucose concentration or interstitial fluid glucose concentration).

14 Claims, 4 Drawing Sheets

Related U.S. Application Data continuation of application No. PCT/US2011/058688, filed on Oct. 31, 2011.

(60) Provisional application No. 61/408,639, filed on Oct. 31, 2010, provisional application No. 61/470,210, filed on Mar. 31, 2011.

(51) Int. Cl.
*A61M 5/142* (2006.01)
*G06F 19/00* (2018.01)
*A61M 5/14* (2006.01)

(52) U.S. Cl.
CPC .......... *G06F 19/00* (2013.01); *G06F 19/3462* (2013.01); *G06F 19/3468* (2013.01); *G16H 50/50* (2018.01); *A61M 2005/1402* (2013.01); *A61M 2005/14208* (2013.01); *A61M 2202/07* (2013.01); *A61M 2205/52* (2013.01); *A61M 2230/201* (2013.01)

(56) References Cited

U.S. PATENT DOCUMENTS

| | | |
|---|---|---|
| 2008/0208113 A1 | 8/2008 | Damiano et al. |
| 2008/0269714 A1 | 10/2008 | Mastrototaro et al. |
| 2008/0319384 A1 | 12/2008 | Yodfat et al. |
| 2010/0082167 A1 | 4/2010 | Haueter et al. |
| 2010/0137788 A1 | 6/2010 | Braithwaite et al. |
| 2010/0256466 A1 | 10/2010 | Shekalim et al. |
| 2010/0262117 A1 | 10/2010 | Magni et al. |

FOREIGN PATENT DOCUMENTS

| | | |
|---|---|---|
| JP | 2010523167 A | 7/2010 |
| JP | 2010531678 A | 9/2010 |
| JP | 2010531707 A | 9/2010 |
| WO | 2006124716 A3 | 11/2006 |
| WO | 2008057384 A3 | 5/2008 |
| WO | 2008094249 A1 | 8/2008 |
| WO | 2008114254 A1 | 9/2008 |
| WO | 2008157780 A1 | 12/2008 |
| WO | 2009001349 A1 | 12/2008 | ns
BLOOD GLUCOSE CONTROL SYSTEM

STATEMENT OF GOVERNMENT RIGHTS

This invention was made with Government Support under Contract No. DK085633 awarded by the National Institutes of Health. The US Government has certain rights in the invention.

BACKGROUND

Standard-of-care insulin therapies for regulating blood glucose in diabetes typically involve either multiple daily subcutaneous injections or subcutaneous infusion with an insulin pump. In the case of the former, daily boluses of long-acting insulin formulations, which release slowly into the blood stream, are used to provide the subject's basal metabolic insulin requirement and boluses of rapid-acting insulin formulations, which absorb rapidly into the blood stream, are used to provide insulin for meals or to treat hyperglycemia. In the case of insulin pump therapy, either regular human recombinant insulin is used or, more typically, one of several rapid-acting insulin formulations is used to provide both basal and bolus therapy. In this case, a pre-programmed basal insulin infusion rate (or a preprogrammed daily "profile" containing several different basal insulin infusion rates that vary throughout the day) is prescribed and administered automatically by the insulin pump throughout the day, and individual boluses to insulin for meals or to treat hyperglycemia are administered with the insulin pump manually by the subject as needed. The preprogrammed basal insulin infusion rate (or pre-programmed daily basal insulin infusion rate profile) can be changed to (or temporarily overridden with) a different infusion rate by the subject, but once implemented, will execute the prescribed infusion rate without knowledge of, or regard to, instantaneous glucose levels from a continuous glucose monitoring device.

Clemens & Hough (U.S. Pat. No. 4,464,170) introduced the idea of using glucose-sensor data (obtained from a device capable of frequently sampling blood glucose concentration levels) to modulate the basal infusion rate relative to a previously prescribed basal insulin infusion rate during online operation of an autonomous glucose control system. Their strategy attempts to control drift in blood glucose away from a set point blood glucose value by considering the slope of the least squares fit to past blood glucose values. The method is described in the context of intravenous insulin infusion in an in-patient setting and implicitly assumes that insulin administered by the controller appears instantly in blood.

SUMMARY

Techniques are disclosed for adaptation of certain drug-administration parameters that control insulin delivery in a blood glucose control system. In one aspect, a technique provides relatively long-term adaptation of a nominal basal infusion rate around which the infusion of basal insulin is automatically modulated. Use of the method can provide not only a daily control regime tailored to an individual patient, but one that can also adapt to longer-term changes in a patient's needs such as may arise from growth, illness, hormonal fluctuations, physical activity, aging, etc. In another aspect, another technique provides similar adaptation of the size of bolus insulin provided at mealtimes, offering the potential of overall better glycemic control in individuals and also providing the adaptation to longer-term changes in a patient's needs. Both techniques may employ adaptation calculations using a receding-horizon window of recent values of the adapted parameter. In yet another aspect, the system also delivers doses of a counter-regulatory agent such as glucagon to the subject in response, at least in part, to information about estimated accumulation of exogenously infused insulin (either subcutaneously, intramuscularly, intraperitoneally, or intravenously) and/or the effect that insulin might have on glucose levels (either blood glucose concentration or interstitial fluid glucose concentration).

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

The contents of the following US provisional patent applications are incorporated herein by reference:
1. U.S. 61/408,639 filed Oct. 31, 2010
2. U.S. 61/470,210 filed Mar. 31, 2010

Additionally, the contents of the following US non-provisional patent application is incorporated herein by reference:
1. U.S. Ser. No. 13/870,634 filed Apr. 25, 2013

Figure 1:
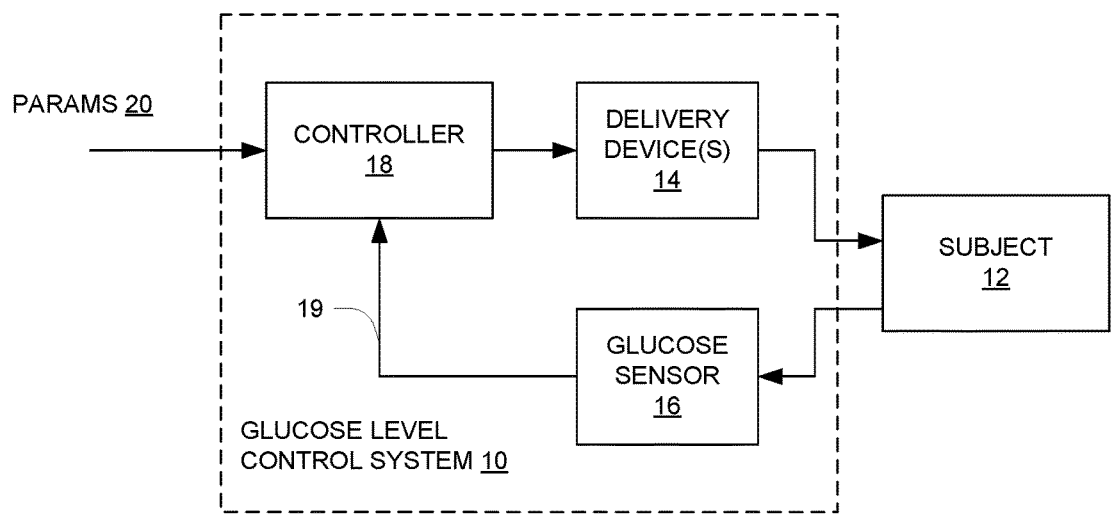
FIG. 1 is a block diagram of a blood glucose control system.

FIG. 1 illustrates an automated control system 10 for regulating the blood glucose level of an animal subject (subject) 12, which may be a human. The subject 12 receives doses of insulin from one or more delivery devices 14, for example infusion pump(s) coupled by catheter(s) to a subcutaneous space of the subject 12. As described below, the delivery devices 14 may also deliver a counter-regulatory agent such as glucagon for control of blood glucose level under certain circumstances. For the delivery of both insulin and glucagon, the delivery devices 14 are preferably mechanically driven infusion mechanisms having dual cartridges for insulin and glucagon respectively. In the present description, reference is made to glucagon specifically, but it is to be understood that this is for convenience only and that other counter-regulatory agents may be used. Similarly, the term "insulin" herein is to be understood as encompassing all forms of insulin-like substances including natural human or animal insulin as well as synthetic insulin in any of a variety of forms (commonly referred to as an "insulin analogs").

A glucose sensor 16 is operatively coupled to the subject 12 to continually sample a glucose level of the subject 12. Sensing may be accomplished in a variety of ways. A controller 18 controls operation of the delivery device(s) 14 as a function of a glucose level signal 19 from the glucose sensor 16 and subject to programmed input parameters (PARAMS) 20 which may be provided by the patient/user. One feature of the disclosed technique is its ability to perform without receiving explicit information regarding either meals that the subject 12 has ingested or any other "feedforward" information. One necessary input parameter is the weight of the subject 12. Another externally provided parameter is a "setpoint" which, as described below, establishes a target blood glucose level that the system 10 strives to maintain.

The controller 18 is an electrical device with control circuitry that provides operating functionality as described herein. In one embodiment, the controller 18 may be realized as a computerized device having computer instruction processing circuitry that executes one or more computer programs each including respective sets of computer instructions. In this case the processing circuitry will generally include one or more processors along with memory and input/output circuitry coupled to the processor(s), where the memory stores computer program instructions and data and the input/output circuitry provides interface(s) to external devices such as the glucose sensor 16 and delivery device(s) 14.

Figure 2:
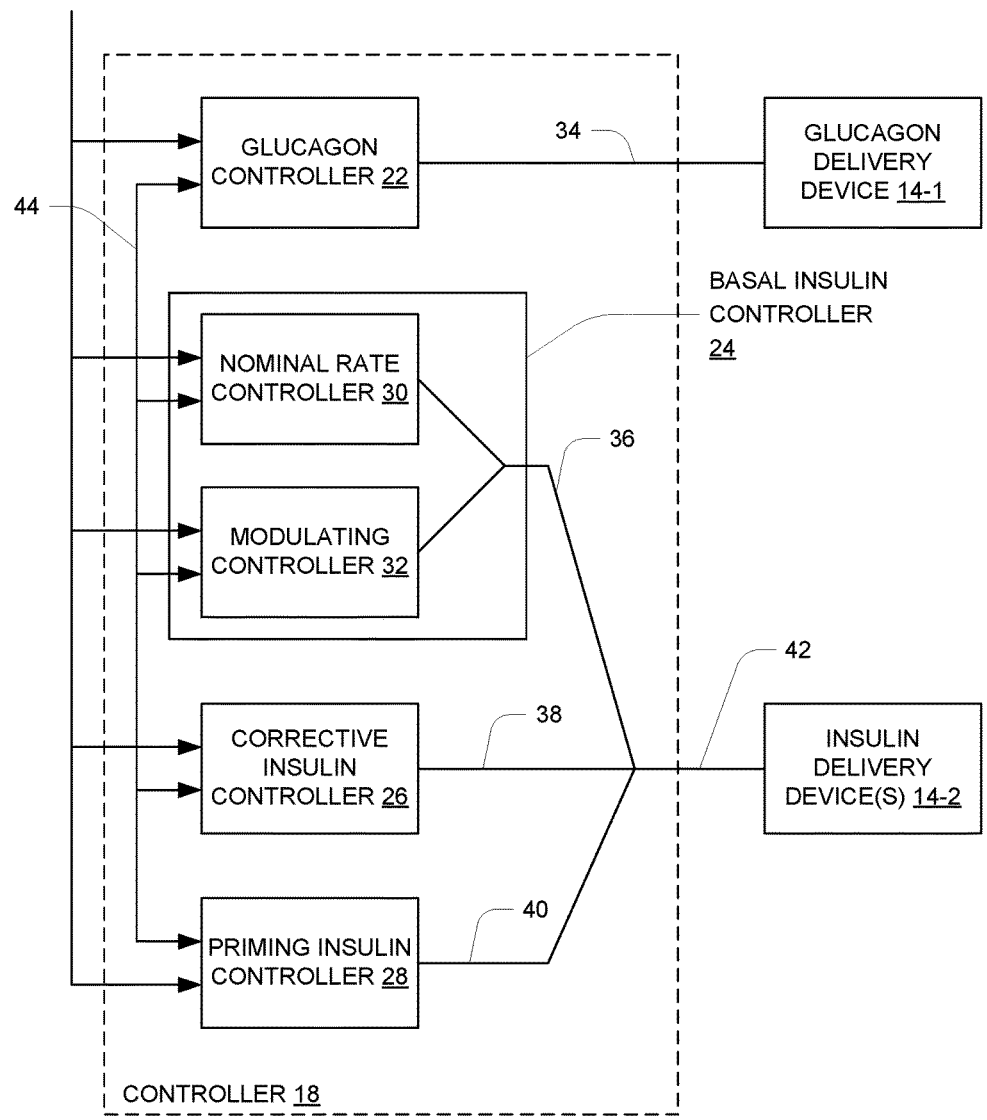
FIG. 2 is a block diagram of a controller.

FIG. 2 shows the structure of the controller 18. It includes four separate controllers, namely a glucagon controller 22, basal insulin controller 24, corrective insulin controller 26, and priming insulin controller 28. The basal insulin controller 24 includes a nominal rate controller 30 and a modulating controller 32. As shown, the glucagon controller 22 generates a glucagon dose control signal 34 provided to a glucagon delivery device 14-1. Respective outputs 36-40 from the controllers 24-28 are combined to form an overall insulin dose control signal 42 provided to insulin delivery device(s) 14-2. As shown, the output signal 36 itself is formed by a combination of respective outputs of the nominal rate controller 30 and modulating controller 32. The insulin delivery device(s) 14-2 may include devices tailored to deliver different types and/or quantities of insulin, with the exact configuration being known to and under the control of the controllers 24-28. For ease of description the collection of one or more insulin delivery devices 14-2 is referred below to in the singular as an insulin delivery device 14-2.

Also shown in FIG. 2 are input/output signals of the various controllers, including the glucose level signal 19 and parameters 20 as well as a set of inter-controller signals 44. The inter-controller signals 44 enable communication of information from one controller, where the information is developed or generated, to another controller where the information is used for that controller's control function. Details are provided in the description of the control functions below.

The corrective controller 26 regulates blood glucose level using an MPC cost function in a manner described in US patent publication 2008/0208113A1, the contents of which are incorporated by reference herein.

Referring to the Clemens & Hough technique referred to above, while this approach may have practical utility in the setting of intravenous insulin infusion, it is susceptible to uncontrolled escalation of insulin dosing in an outpatient setting where insulin infusion would likely occur subcutaneously resulting in delayed absorption of insulin into blood. Such an approach would potentially have to be overridden often to limit escalation of insulin dosing in such a setting. Another limitation of the method is that it only captures one time scale (equal to the time associated with obtaining a fixed number of consecutive past glucose levels); it does not account for long-time variations in the subject's basal insulin requirement.

Rather than relying solely on the previously prescribed basal insulin infusion rate, which is particularly vulnerable to a run-away escalation of insulin dosing whenever subcutaneous insulin administration is used, an alternative method (herein referred to as Method 1) modulates the basal insulin infusion rate around a fixed "nominal" basal infusion rate, which is determined prior to initiating online operation of the glucose control system (e.g. based on the subject's weight or based on previous open- or closed-loop control results in the subject). This can be described as follows: Through any manner by which automated insulin infusion may be controlled online (such as through a model predictive control strategy, a proportional-integral-derivative control strategy, fuzzy logic, neural networks, or some other control strategy), there can be added a basal infusion rate of insulin delivered when control or corrective doses of insulin are not otherwise indicated. Basal-rate infusion typically uses smaller but more frequent doses than priming or control doses used to treat meals or hyperglycemic excursions in glucose concentration levels. A fixed nominal basal infusion rate can be initially prescribed (i.e. just before initiating online operation of closed-loop control) and then modulated by its own control algorithm, or it can be prescribed in advance in the form of a fixed basal infusion rate profile that follows the same pattern from day to day (or week to week), and is then modulated online. The basal insulin infusion rate is automatically modulated around the fixed nominal infusion rate using any of a variety of control strategies including, but not limited to, model predictive control, proportional-integral-derivative control, fuzzy logic, neural networks, etc.

As another distinction from the method described by Clemens & Hough, the modulation of the basal insulin infusion rate described here should be constrained to fall within minimum and maximum values around the nominal basal infusion rate so as to prevent a run-away escalation of insulin dosing. The maximum value may be, for example, some constant multiple of the fixed nominal basal infusion rate.

Although Method 1 represents an improvement upon the technique of Clemens & Hough by preventing runaway escalation of insulin dosing through constraining the maximum instantaneous basal infusion rate, it only captures one time scale, i.e. that which is associated with the sampling interval between glucose measurements. Method 1 can be further improved with an alternative method (herein referred to as Method 2) that allows the nominal basal infusion rate itself to vary over time, which, in turn, allows the instantaneous basal infusion rate to inherit a second longer time scale capable of capturing physiological variations in the subject's basal metabolic insulin requirement. Whereas the instantaneous basal infusion rate can change rapidly on the very short time scale associated with the sampling interval between glucose measurements, the introduction of a nominal basal infusion rate that varies over time more slowly than the instantaneous basal infusion rate provides a second degree of freedom that can capture physiological drift in a subject's basal metabolic insulin requirement while still constraining the maximum instantaneous basal infusion rate to be some constant multiple of the nominal basal infusion rate, and thereby preventing run-away escalation of basal insulin dosing.

Figure 3:
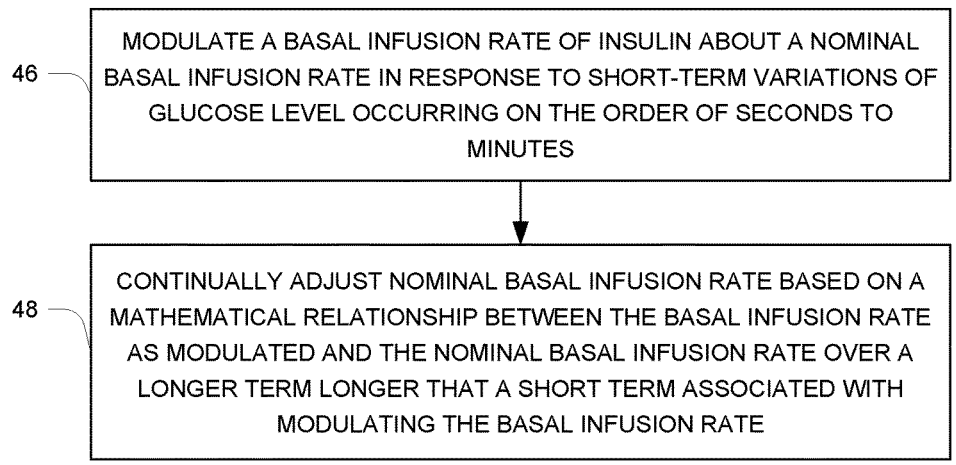
FIG. 3 is a flow diagram of a first method of operation of the system.

In particular, referring to FIG. 3, the basal insulin controller 24 generates the insulin dose control signal 42 via its output signal 36 in response to the glucose level signal 19. At 46, the controller 24 modulates a basal infusion rate of insulin about a nominal basal infusion rate in response to short-term variations of glucose level occurring on the order of seconds to minutes (referred to as a "sampling interval" below). At 48, the controller 24 continually adjusts the nominal basal infusion rate based on a mathematical relationship between the basal infusion rate as modulated and the nominal basal infusion rate over a longer term than a short term (e.g., sampling interval) associated with modulating the basal infusion rate.

As an example of one embodiment of Method 2, the nominal basal infusion rate of insulin (or an insulin-like agent) can be initially prescribed at t=0 as $\mu_0$. Then, the nominal basal infusion rate, $\bar{\mu}(t)$, can begin being calculated online (and updated at each sampling interval, $\delta t$) as a scalar multiple of the moving integral average value of the instantaneous basal infusion rate, $\mu(t) \geq 0$, over the time interval, $\Delta t$, such that $$\bar{\mu}(t + \delta t) = \frac{\alpha}{\Delta t} \int_{t-\Delta t}^{t} \mu(\tau) d\tau, \ t \geq \Delta t \quad (1)$$

where $\alpha$ is a scaling parameter. Alternatively, the implementation could be performed in discrete time, where k is the index of the current time step, $\delta t$ is the size of the discrete time step (i.e. an index increment of 1), and $N=\Delta t/\delta t$ is the size of the time interval, giving the alternative form for the instantaneous dynamic nominal basal infusion rate of:

$$\bar{\mu}_{k+1} = \frac{\alpha}{N} \sum_{j=k-N}^{k} \mu_j, \ k \geq N \quad (2)$$

The instantaneous basal infusion rate, $\mu(t)$, or $\mu_k$ in discrete time, is allowed to modulate around the instantaneous dynamic nominal value, $\bar{\mu}(t)$, or $\bar{\mu}_k$ in discrete time. Specifically, $\mu(t)$ (or $\mu_k$) can be increased or decreased when the glucose level rises or falls below a set-point glucose value or a set range of glucose values. Modulation of $\mu(t)$ around $\bar{\mu}(t)$ (or $\mu_k$ around $\bar{\mu}_k$) can also be affected by the rate of increase or decrease of the glucose level. More sophisticated control methods could also be employed to determine the modulation of $\mu(t)$ around $\bar{\mu}(t)$ (or $\mu_k$ around $\bar{\mu}_k$), such as, but not limited to, using a model predictive control strategy, a proportional-integral-derivative control strategy, fuzzy logic, neural networks, or some other control strategy.

Figure 4:
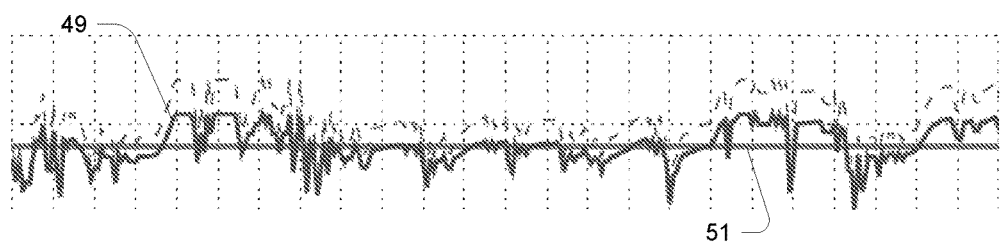
FIGS. 4-5 are waveform diagrams depicting certain results of operation according to FIG. 3.
Figure 5:
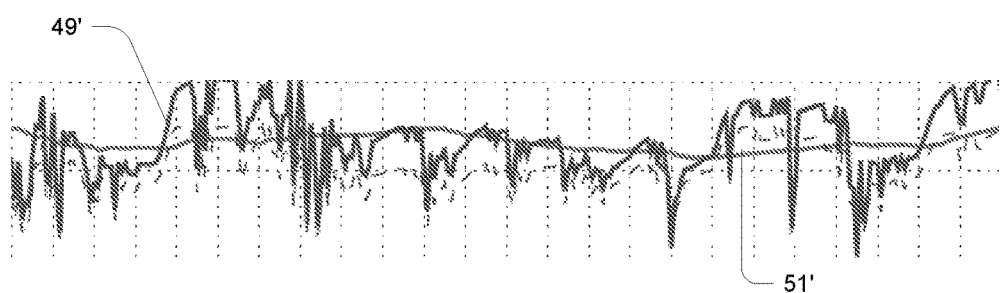

FIGS. 4 and 5 provide an illustration of the effect of the method of FIG. 3. FIG. 4 shows a modulated basal infusion rate 49 about a fixed constant nominal basal infusion rate 51. FIG. 5 shows a modulated basal infusion rate 49' about a continually adapted nominal basal infusion rate 51'.

Thus, Method 2 offers an approach that is capable of both preventing run-away escalation of insulin dosing (by constraining the maximum instantaneous basal infusion rate to be some constant multiple of the dynamic nominal basal infusion rate) as well as capturing multiple time scales for adaptation. In particular, $\mu(t)$ (or $\mu_k$) is allowed to vary rapidly online over a time scale $\delta t$ (which might be on the order of minutes in real time and O(1) in discrete time), whereas $\bar{\mu}(t)$ (or $\bar{\mu}_k$) around which $\mu(t)$ (or $\mu_k$) modulates, varies more slowly online over a time scale $\Delta t$ (which might be on the order of hours in real time and O(N) in discrete time).

The approach according to Method 2 sets the instantaneous dynamic nominal basal infusion rate, $\bar{\mu}(t)$ (or $\bar{\mu}_k$), equal to a constant multiple of the average nominal value over some receding time interval, $\Delta t$ (or N). In an alternative embodiment (herein referred to as Method 3), the instantaneous dynamic nominal basal infusion rate can be adapted online so as to enforce a constant ratio over the interval $\Delta t$ (or N) between all of the modulated instantaneous basal infusion rates, $\mu(t)$ (or $\mu_k$), and their corresponding moving average dynamic nominal basal infusion rates, $\bar{\mu}(t)$ (or $\bar{\mu}_k$). In other words, to enforce such a constant ratio of $\beta$, then $$\bar{\mu}(t + \delta t) = \bar{\mu}(t)\left(\frac{\beta}{\Delta t}\int_{t-\Delta t}^{t}\frac{\mu(\tau)}{\bar{\mu}(\tau)}d\tau\right), \ t \geq \Delta t \quad (3)$$

or in discrete time, $$\bar{\mu}_{k+1} = \bar{\mu}_k\left(\frac{\beta}{N}\sum_{j=k-N}^{k}\frac{\mu_j}{\bar{\mu}_j}\right), \ k \geq N \quad (4)$$

In the same manner as described above for Method 2, in Method 3, the instantaneous basal infusion rate, $\mu(t)$ (or $\mu_k$), is allowed to modulate around the instantaneous dynamic nominal value, $\bar{\mu}(t)$ (or $\bar{\mu}_k$ in discrete time).

In either implementation, i.e. according to either Method 2 (Equations (1) and (2)) or Method 3 (Equations (3) and (4)), the determined dynamic nominal basal infusion rate can be limited between a global minimum value, $\bar{\mu}_L$, and a global maximum value, $\bar{\mu}_H$, i.e. $\bar{\mu}_L \leq \mu(t) \leq \bar{\mu}_H$ in Equations (1) and (3) or $\bar{\mu}_L \leq \bar{\mu}_k \leq \bar{\mu}_H$ in Equations (2) and (4). The implementation of Method 2 or Method 3 described above could also start taking effect gradually online (e.g. linearly) from t=0 (or k=0) until the interval size, $\Delta t$ (or N), is reached online.

Methods 2 or 3 can equally be applied to adapt online a nominal basal-rate profile that includes a set of different nominal basal-rate levels that could be prescribed for different time periods of the day or for different days, or both. The individual nominal basal-rate levels within a (daily or semi-daily) profile could be of different time durations and their durations or their starting and ending times could also vary from day to day. The individual nominal basal-rate levels could be prescribed globally for all individuals or could be prescribed differently for different individuals, and could be based on previous control results (e.g. open-loop or closed-loop settings for each individual subject).

An example of this embodiment is to use the method above to adapt an initially prescribed $\mu_0:=\mu_0(t)$ (or $\mu_{0k}$ in discrete time) that could be represented as a piecewise function. As such, Equations (1) or (3) in real time (or Equations (2) and (4) in discrete time) could be applied to each of the individual nominal basal-rate levels within the piecewise function. At the time juncture between consecutive nominal basal-rate levels, the transition could occur as a discontinuous jump from the nominal basal-rate level of the elapsed time period to the nominal basal-rate level of the entered time period. Alternatively, the transition could occur in a gradual fashion (e.g. linearly) over a certain time period that could be fixed or variable. Moreover, the previous adaptation history of individual nominal basal-rate levels could be inherited upon subsequently encountering the same or an overlapping time period or time juncture (e.g. on the next day or after a number of days). The online instantaneous basal infusion rate could then be a modulation based on the current nominal basal-rate level pertaining to the current time period online, or based on adjacent nominal basal-rate levels during a transition between nominal basal-rate levels online.

All of the methods described above could be used in the in-patient (e.g. critical care units or general wards) or out-patient settings and could be used in the context of an autonomous or semi-autonomous closed-loop blood-glucose control system. The methods could also be used in open-loop systems where only the basal infusion rate is automatically controlled and all other doses are manually administered. In any case, modulation of the instantaneous basal infusion rate, $\mu(t)$ (or $\mu_k$), and long-time adaptation of those modulations around the moving average dynamic nominal basal infusion rate, $\bar{\mu}(t)$ (or $\bar{\mu}_k$), will involve a sensor-augmented infusion system that is capable of responding to frequent (typically every 5-15 minutes) glucose measurements from a continuous glucose monitor or other glucose measuring device. Another utility involves utilizing the basal infusion rates obtained with any of these methods online in a sensor-augmented infusion system to inform open-loop basal-rate profile settings that could be prescribed for the subject when the system is (temporarily or permanently) not driven by the glucose sensor, such as during periods of temporary interruptions or dropouts in the glucose sensor signal, or for open-loop insulin infusion therapy.

In another aspect, a method is shown for automatically adapting doses of infused insulin or insulin-like agents (either subcutaneously, intramuscularly, intraperitoneally, or intravenously) where the doses are intended to partially or fully compensate for food (carbohydrate) consumption. The doses can be administered prior to, during, or after food consumption, or could be split across these times. The online adaptation method can automatically tune these meal-time insulin doses on an individual basis and can automatically adjust them over time to respond to long-time changes in the individual's insulin requirement, such as might occur over a period of weeks, months, or years due to developmental changes (e.g. due to hormonal changes that occur during puberty or menopause), or as might occur over a period of hours, days, or weeks due to transient changes (e.g. due to circadian hormonal fluctuations, intercurrent illness, physical activity, or emotional state).

Standard-of-care insulin therapies for regulating blood glucose in diabetes typically involve either multiple daily subcutaneous injections or subcutaneous infusion with an insulin pump. Typically, combinations of "basal and bolus" insulin are administered to meet the subject's basal metabolic insulin requirement as well to regulate hyperglycemia; additional "meal bolus" doses (also referred to herein as "priming doses") are added to provide insulin for food consumption. Insulin doses intended to compensate for meals are usually estimated on an individual basis based on the quantity and content (carbohydrate and other) of the food, in conjunction with an estimate of the individual's so-called "insulin-to-carbohydrate ratio", among other factors such as the time of the day, physical activity, health state, emotional state, etc. The correct meal-bolus insulin amount, therefore, could vary significantly among individuals as well as within an individual. Moreover, the amount of meal-bolus insulin is often a major determinant of how well an individual is able to control their blood glucose. We provide a method that would automatically and continually adjust meal-time doses of insulin (intended to partially or fully compensate for food consumption), based on the individual's response to previous meal doses.

Figure 6:
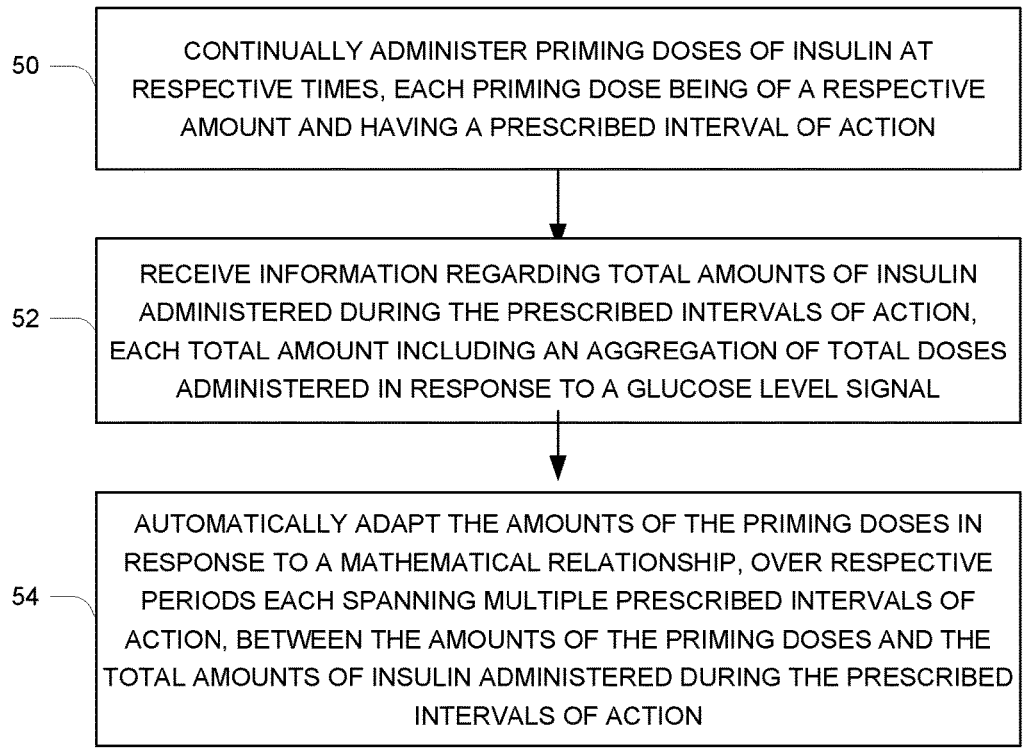
FIGS. 6-7 are flow diagrams of additional methods of operation of the system.

In particular, referring to FIG. 6, at 50 the priming insulin controller 28 continually administers priming doses of insulin at respective times, each priming dose being of a respective amount and having a prescribed interval of action. At 52, the controller 28 receives information (e.g., from the other controllers 24-26 via signals 44) regarding total amounts of insulin administered during the prescribed intervals of action, each total amount including an aggregation of total doses administered in response to a glucose level signal. At 54, the controller 28 automatically adapts the amounts of the priming doses in response to a mathematical relationship, over respective periods each spanning multiple prescribed intervals of action, between the amounts of the priming doses and the total amounts of insulin administered during the prescribed intervals of action.

As an example of one embodiment of the method of FIG. 6, the effective instantaneous dynamic meal-time bolus (which can be split into a number of doses), $B^m(t)$ (or $B_k^m$ in discrete time), corresponding to meal m (or corresponding to a time interval m) on any given day t (or k in discrete time), can be adapted online so as to enforce, on average, over a time horizon of $\Delta t$ (or N in discrete time) days (e.g. 1 week or 1 month long) a certain target ratio, $\beta^m$, between the magnitudes of $B^m(t)$ (or $B_k^m$) and their corresponding overall insulin amount around that meal (or time interval), $P^m(t)$ (or $P_k^m$), where $P^m(t)=B^m(t)+C^m(t)$ (or $P_k^m=B_k^m+C_k^m$), where $C^m(t)$ (or $C_k^m$) includes all prandial and post-prandial insulin (other than $B^m(t)$ (or $B_k^m$)) that was given by the control system for that meal (or corresponding to time interval) m, computed over a certain prandial and post-prandial time interval of $\delta t$ hours (e.g. 5 hours). In other words, to enforce (on average) a ratio $\beta^m$ (e.g. 50-75%) between $B^m(t)$ and overall dosing $P^m(t)$ around meal (or time interval) m on day t+1, then $$B^m(t+1) = \beta^m B^m(t) \left( \frac{1}{\Delta t} \int_{t-\Delta t}^{t} \frac{B^m(\tau)}{B^m(\tau) + C^m(\tau)} d\tau \right)^{-1}, \quad t \geq \Delta t \quad (5)$$

or in discrete time, $$B_{k+1}^m = \beta^m B_k^m \left( \frac{1}{N} \sum_{j=k-N+1}^{k} \frac{B_j^m}{B_j^m + C_j^m} \right)^{-1}, \quad k \geq N \quad (6)$$

The target ratios, $\beta^m$, can also be varied over time, i.e. $\beta^m:=\beta^m(t)$ (or $\beta_k^m$). Moreover, different time intervals $\delta t$ could be used in the computations of $C^m(\tau)$ (or $C_j^m$) for different meals m (or different time intervals m) of the day. Furthermore, the implementation could start taking effect gradually online (e.g. linearly or stepwise) from the first day at t=1 (or k=1) until the interval size $\Delta t$ (or N) is reached online. Alternatively, the method can take its full effect from the start while transiently using n=1, 2, 3, . . . in lieu of the intended full interval size N, until n reaches N, after which the implementation takes on its steady form of a "moving average" over its full "receding horizon" N. Finally, the interval length $\Delta t$ (or N) could also be made variable with m and/or time t (or k).

The method described above could be used in the in-patient (e.g. critical care units or general wards) or out-patient settings and could be used in the context of an autonomous or semi-autonomous closed-loop blood-glucose control system. Feedback from the use of this method during autonomous or semi-autonomous control could also be used to inform open-loop systems, that may or may not be augmented with an online glucose sensor.

In another aspect, a method is shown for automatically modulating doses of infused glucagon (either subcutaneously, intramuscularly, intraperitoneally, or intravenously) that relies in part on information about the estimated accumulation of exogenously infused insulin (either subcutaneously, intramuscularly, intraperitoneally, or intravenously) and/or the effect that insulin might have on glucose levels (either blood glucose concentration or interstitial fluid glucose concentration). Through any manner by which automated glucagon infusion may be controlled online (such as through a model predictive control strategy, a proportional-derivative control strategy, or some other control strategy), there can be derived a mathematical formulation by which the control dose of glucagon depends in some manner upon the estimated accumulation of exogenously infused insulin. Specifically, the particular formulation employed would cause the glucagon infusion rate (or delivery amount) to be higher at times when the accumulation of infused insulin is relatively higher than it would be at times when the accumulation of infused insulin is relatively lower.

Figure 7:
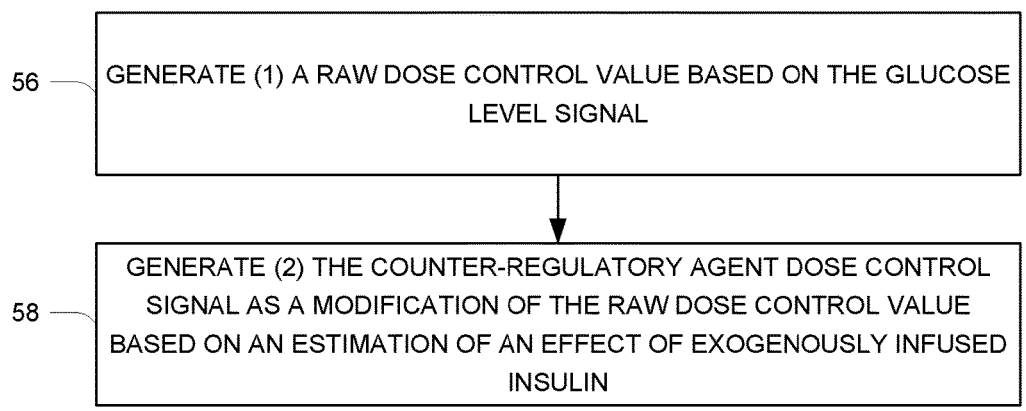

In particular, referring to FIG. 7, at 56 the glucagon controller 24 generates the counter-regulatory agent dose control signal 34 by performing a calculation generating (1) a raw dose control value based on the glucose level signal, and at 58 generating (2) the counter-regulatory agent dose control signal as a modification of the raw dose control value based on an estimation of an effect of the exogenously infused insulin.

As an example of one embodiment of the method of FIG. 7, glucagon could be controlled with using a proportional-derivative (PD) control strategy where the control doses thus determined would be scaled using a multiplying factor that is proportional to (either linearly or nonlinearly) the estimated accumulation of exogenously infused insulin. Whenever the glucose concentration falls below some set point, or whenever the glucose concentration falls below some threshold value, $\beta$, with a sufficiently rapid descent, a glucagon dose, $G_{dose}(t)$ might be triggered as follows:

$$G_{dose}(t)=f(i_e(t))\{k_p(\beta-y_t)+k_d(y_{t-1}-y_t)/T_s\};\ 0\leq G_{dose}(t)\leq G_{max}, \quad (7)$$

where $G_{max}$ is the maximum allowable glucagon dose (which may be infinite), t is in discrete time, $k_p$ is the proportional gain, $k_d$ is the derivative gain, $T_s$ is the sampling period, $i_e(t)$ is the estimated accumulation of exogenously infused insulin, and $f(i_e(t))$ is some specified function of $i_e(t)$ that has units of $G_{dose}(t)$. An example $f(i_e(t))$ might be a sigmoidal function that is near unity whenever $i_e(t)$ is less than some factor times some estimated nominal or baseline value of the plasma insulin level and then begins to increase significantly as $i_e(t)$ exceeds this nominal value. Alternatively, in another embodiment, the dependence of $G_{dose}(t)$ on $i_e(t)$ might appear in an additive way, by the introduction of an additional gain parameter, $k_i$, such that $$G_{dose}(t)=k_p(\beta-y_t)+k_d(y_{t-1}-y_t)/T_s+k_i i_e(t);\ 0\leq G_{dose}(t)\leq G_{max}, \quad (8)$$

where $k_i$ might vanish whenever $i_e(t)$ is less than some factor times some estimated nominal or baseline value of the plasma insulin level.

Variations on the above examples might include an additive term, $G_{pending}(t)$, which is deducted from $G_{dose}(t)$, and which represents an estimate of pending subcutaneous glucagon from recent doses. This could be computed, for example, with a function such as $$G_{pending}(t) = \sum_{k=1}^{90/T_s} G_{dose}(t-k)\left(\frac{1}{2}\right)^{kT_s G_{1/2}} \quad (9)$$

where $G_{1/2}$ is an estimate of the average half life of subcutaneous doses of glucagon. Note that the estimate $G_{pending}(t)$ limits unnecessary subcutaneous accumulation of glucagon. Thus, including $G_{pending}(t)$ in Equations (7) and (8) could provide the alternate forms given by $$G_{dose}(t)=f(i_e(t))\{k_p(\beta-y_t)+k_d(y_{t-1}-y_t)/T_s-G_{pending}(t)\};\ 0\leq G_{dose}(t)\leq G_{max}, \quad (10)$$

$$G_{dose}(t)=k_p(\beta-y_t)+k_d(y_{t-1}-y_t)/T_s+k_i i_e(t)-G_{pending}(t);\ 0\leq G_{dose}(t)\leq G_{max}, \quad (11)$$

Alternatively, $G_{pending}(t)$ might appear in an additive way, by the introduction of an additional gain parameter, $k_g$, such that $G_{pending}(t)$ in Equations (10) and (11) might be replaced by $k_g g_e(t)$, where $g_e(t)$ is the estimated accumulation of exogenously infused glucagon.

In yet another embodiment, the control doses of glucagon, $G_{dose}(t)$, may employ a model predictive control (MPC) strategy, where the modulation of glucagon doses due to the estimated accumulation of exogenously infused insulin, $i_e(t)$, could be achieved using an outer scaling function (similar to the function $f(i_e(t))$ in Equation (7)). For example, the control doses of glucagon may be computed as:

$$G_{dose}(t)=g(i_e(t))u_t;\ 0\leq G_{dose}(t)\leq G_{max}, \quad (12)$$

where $u_t$ is the MPC glucagon dose signal and $g(i_e(t))$ is an outer scaling that is similar or identical to $f(i_e(t))$ in that it is some function that is near unity whenever $i_e(t)$ is less than some factor times some estimated nominal or baseline value of the plasma insulin level and is significantly higher when as $i_e(t)$ exceeds this nominal value. One example for computing $u_t$ is using an MPC cost function such as:

$$J = \sum_{k=N_d}^{N_m} \delta_k \|C(r_{t+k} - y_{t+k})\|^2 + \sum_{k=0}^{N_u} \lambda_k (\Delta u_{t+k})^2 \quad (13)$$

where $u_t$ denotes the MPC glucagon dose signal, $y_t$ the glucose concentration signal, $r_t$ the reference set point signal, $N_d$ and $N_m$ are respectively the minimum and maximum (output) prediction costing horizon limits, $N_u$ the control horizon bound, m the weighting on prediction error, and $\lambda_n$ the weighting on control signals. The glucose concentration, $y_t$, and the glucagon dose signal, $u_t$, could also be related by subject model. Upon solving Equation (13) for the MPC glucagon dose signal, $u_t$, the outer scaling with $g(i_e(t))$ could then be applied as per Equation (12) to compute the control doses of glucagon, $G_{dose}(t)$. Alternatively, the control doses of glucagon, $G_{dose}(t)$, could be based on the MPC glucagon dose signal, $u_t$, and an incorporation of the effect of $i_e(t)$ in an additive way, by the introduction of a gain parameter, $k_i$, such that $$G_{dose}(t)=u_t+k_i i_e(t));\ 0\leq G_{dose}(t)\leq G_{max}, \quad (14)$$

where $k_i$ might vanish whenever $i_e(t)$ is less than some factor times some estimated nominal or baseline value of the plasma insulin level.

Furthermore, the control doses of glucagon, $G_{dose}(t)$, could also take into account the accumulation of glucagon from past glucagon doses. This could be handled by computing a quantity $G_{pending}(t)$ similar to that described in Equation (9) and computing the control doses of glucagon as per $$G_{dose}(t)=g(i_e(t))\{u_t-G_{pending}(t)\};\ 0\le G_{dose}(t)\le G_{max}, \qquad (15)$$

or $$G_{dose}(t)=u_t+k_t(i_e(t))-G_{pending}(t);\ 0\le G_{dose}(t)\le G_{max}, \qquad (16)$$

Alternatively, $G_{pending}(t)$ might appear in an additive way, by the introduction of an additional gain parameter, $k_g$, such that $G_{pending}(t)$ in Equations (15) and (16) might be replaced by $k_g g_e(t)$, where $g_e(t)$ is the estimated accumulation of exogenously infused glucagon.

Another option for accounting for the accumulation of glucagon from past doses is by augmenting the MPC cost function in Equation (13) with a mathematical formulation that estimates the accumulation of exogenous glucagon in a manner similar to that described in US patent publication 2008/0208113A1. Such an augmentation could take into account the accumulation of glucagon in both the administration site(s) as well as in plasma and could be based on pharmacokinetics of the administered glucagon pertaining to the method or route of administration as well as to the specific constituents present in the glucagon solution, including the type of glucagon or glucagon analog itself. With such an augmentation in effect, the MPC glucagon dose signal, $u_t$, becomes an augmented MPC glucagon dose signal, $\mu'_t$. The augmented MPC glucagon dose signal, $\mu'_t$, could replace the MPC glucagon dose signal, $\mu_t$, in both Equations (12) and (14) to provide the control doses of glucagon, $G_{dose}(t)$.

Other control signals could replace the MPC glucagon dose signal, $u_t$, in Equations (12), (14), (15), or (16) and could be based on another algorithm such as a neural network, or a fuzzy logic, or a standard optimization algorithm.

In all the formulations above, the function $i_e(t)$ may be computed by any manner by which the accumulation of exogenously infused insulin might be estimated.

It will be appreciated that the present invention may be embodied as an overall system such as shown in FIG. 1, as an overall method, as a controller such as shown in FIG. 2, and as methods performed by a controller such as shown in FIGS. 3-5. With respect to the methods performed by a controller, the methods may be performed by computer program instructions executed by generic controller hardware including memory, a processing or execution unit, and input/output circuitry. The instructions may be provided to the controller from a computer-readable medium such as semiconductor memory, magnetic memory (e.g. magnetic disk), optical memory (e.g. optical disk such as CD, DVD), etc.

While various embodiments of the invention have been particularly shown and described, it will be understood by those skilled in the art that various changes in form and details may be made therein without departing from the scope of the invention as defined by the appended claims.

What is claimed is:

1. A sensor-driven glucose control system, comprising:
   an insulin delivery device operative in response to an insulin dose control signal to infuse insulin into the subject; and
   a controller operative to generate the insulin dose control signal by:
   (1) continually administering priming doses of insulin at respective times, each priming dose being of a respective amount and having a prescribed interval of action;
   (2) receiving information regarding total amounts of insulin administered during the prescribed intervals of action, each total amount including an aggregation of total doses administered in response to a glucose level signal; and
   (3) automatically adapting the amounts of the priming doses in response to a mathematical relationship, over respective periods each spanning multiple prescribed intervals of action, between the amounts of the priming doses and the total amounts of insulin administered during the prescribed intervals of action.

2. A sensor-driven glucose control system according to claim 1, wherein the mathematical relationship includes a target ratio of the amount of each priming dose to the total amount of insulin administered in each prescribed interval of action.

3. A sensor-driven glucose control system according to claim 2, wherein the target ratio has different values over respective time periods of a day, or over different prescribed intervals of action, or both.

4. A sensor-driven glucose control system according to claim 3, wherein the time periods have a regularity associated with timing of food consumption.

5. A sensor-driven glucose control system according to claim 1, wherein each period is defined by a receding-horizon time window extending back from a present time by a predetermined amount of time.

6. A sensor-driven glucose control system according to claim 1, being an autonomous or semi-autonomous control system in which the controller includes a corrective insulin controller that generates the insulin dose control signal in response to the glucose level signal to administer corrective doses of insulin so as to regulate the glucose level signal.

7. A sensor-driven glucose control system according to claim 1, further comprising a counter-regulatory agent delivery device operative to infuse a counter-regulatory agent into the subject in response to a counter-regulatory agent dose control signal, and wherein the controller is operative to generate the counter-regulatory agent dose control signal by performing a calculation generating (1) a raw dose control value based on the glucose level signal, and (2) the counter-regulatory agent dose control signal as a modification of the raw dose control value based on an estimation of an effect of insulin infused into the subject by the insulin delivery device.

8. A method of operating a controller for a sensor-driven glucose control system including an insulin delivery device operative in response to an insulin dose control signal to infuse insulin into the subject, comprising:
   generating the insulin dose control signal to continually administer priming doses of insulin at respective times, each priming dose being of a respective amount and having a prescribed interval of action;
   receiving information regarding total amounts of insulin administered during the prescribed intervals of action, each total amount including an aggregation of total doses administered in response to a glucose level signal; and
   automatically adapting the amounts of the priming doses in response to a mathematical relationship, over respective periods each spanning multiple prescribed intervals of action, between the amounts of the priming doses and the total amounts of insulin administered during the prescribed intervals of action.

9. A method according to claim 8, wherein the mathematical relationship includes a target ratio of the amount of each priming dose to the total amount of insulin administered in each prescribed interval of action.

10. A method according to claim 9, wherein the target ratio has different values over respective time periods of a day, or over different prescribed intervals of action, or both.

11. A method according to claim 10, wherein the time periods have a regularity associated with timing of food consumption.

12. A method according to claim 8, wherein each period is defined by a receding-horizon time window extending back from a present time by a predetermined amount of time.

13. A method according to claim 8, wherein the sensor-driven glucose control system is an autonomous or semi-autonomous control system in which the controller includes a corrective insulin controller that generates the insulin dose control signal in response to the glucose level signal to administer corrective doses of insulin so as to regulate the glucose level signal.

14. A method according to claim 8, wherein the sensor-driven glucose control system further includes a counter-regulatory agent delivery device operative to infuse a counter-regulatory agent into the subject in response to a counter-regulatory agent dose control signal, and wherein the method further includes generating the counter-regulatory agent dose control signal by performing a calculation generating (1) a raw dose control value based on the glucose level signal, and (2) the counter-regulatory agent dose control signal as a modification of the raw dose control value based on an estimation of an effect of insulin infused into the subject by the insulin delivery device.

* * * * *